United States Patent [19]

Kreisel

[11] 4,154,579
[45] May 15, 1979

[54] METHOD AND ARRANGEMENT FOR THE CONTINUOUS QUANTITATIVE INDICATION OF GASEOUS POLLUTANTS IN GASES

[75] Inventor: Wulf-Dieter Kreisel, Staufenberg, Fed. Rep. of Germany

[73] Assignee: U.S. Philips Corporation, New York, N.Y.

[21] Appl. No.: 807,040

[22] Filed: Jun. 16, 1977

[30] Foreign Application Priority Data

Jun. 19, 1976 [DE] Fed. Rep. of Germany ....... 2627606

[51] Int. Cl.$^2$ ............................................. G01N 21/26
[52] U.S. Cl. ..................................... 23/232 E; 422/91
[58] Field of Search ................. 23/230 R, 253 R, 259, 23/232 R, 254 R, 232 E, 254 E

[56] References Cited

U.S. PATENT DOCUMENTS

| | | | |
|---|---|---|---|
| 3,567,392 | 3/1971 | Schulze | 23/254 R |
| 3,578,406 | 5/1971 | Cho et al. | 23/254 R |
| 4,003,708 | 1/1977 | Taguchi et al. | 23/230 R |

Primary Examiner—R. E. Serwin
Attorney, Agent, or Firm—Thomas A. Briody

[57] ABSTRACT

The specification describes a method for the continuous quantitative indication of pollutants in air, in which a reagent solution taken from a storage container is first passed through the reference cell of a photometer, is then mixed in a reaction chamber with the gas to be examined and, dependent on the concentration of the pollutant, is decolorized or colored, is then passed through the measuring cell of the photometer, and is finally collected in a collection container, an indication corresponding to the concentration of pollutant being derived from the output of the photometer, and in which the reagent solution leaving the measuring cell and containing the pollutant is once again supplied to the reaction chamber and produces a more intensive reaction.

8 Claims, 1 Drawing Figure

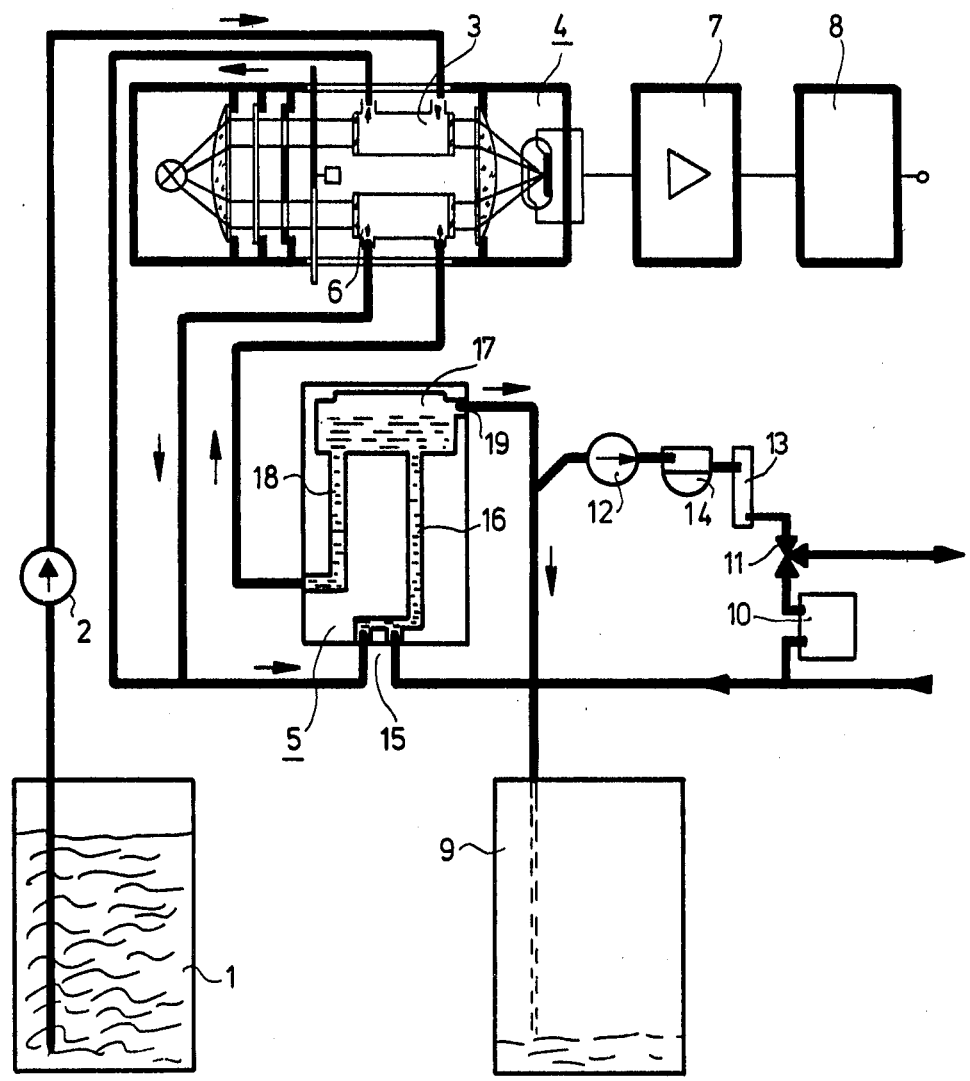

METHOD AND ARRANGEMENT FOR THE CONTINUOUS QUANTITATIVE INDICATION OF GASEOUS POLLUTANTS IN GASES

The invention relates to a method and an arrangement for the quantitative and continuous indication of pollutants, for example $NO_2Cl_2$, $SO_2$, and so on, in gases, for example in air, in which a reagent solution taken from a storage container is first passed through the reference cell of a photometer, is then mixed in a reaction chamber with the gas to be examined and, dependent on the concentration of the pollutant, is decolorized or coloured, is then passed through the measuring cell of the photometer, and is finally collected in a collection container, an indication corresponding to the concentration of pollutant being derived from the output voltage of the photometer.

Such methods and corresponding arrangements are known and are disclosed, for example, in the article "Abgasuberwachung von Industrieanlagen mit einem Betriebsphotometer" published in "Chemie-Ingenieur-Technik", Vol. 10, 1962, pp. 704–708, in particular page 708 and FIG. 6.

Experience has proved that the reaction time of this method is comparatively long, as a result of which admixtures of pollutants which occur suddenly, for example in air, due to damage to industrial plants, are discovered only at a late instant. It is therefore the object of the present invention to improve a method of the kind mentioned in the preamble in such manner that the response time is considerably reduced without, however, increasing the required quantity of reagent solution. The solution according to the invention consists in that the reagent solution leaving the measuring cell and containing the pollutant is once again supplied to the reaction chamber and produces a more intensive reaction.

The remaining reagent solution may be derived from a second outlet of the reaction chamber and be collected in a collection container. The gas present in the solution may be separated and if desired be exhausted to the atmosphere after cleaning in an active-carbon filter, or be supplied again to the reaction chamber by means of a pump as a so-called "zero gas".

For carrying out the method described, the reaction chamber comprises above the vertically arranged reaction track a collection vessel having two outlets of which one is connected to the measuring cell of the photometer and the other of which is in the form of an overflow and is connected to a collection container.

In this manner, the reagent solution is contacted in a cycle several times with the gas to be examined, as a result of which very short response times are achieved while the quantity of fresh reagent solution is very small.

With a supply, for example, of only 20 cm$^3$/hour of fresh reagent solution and approximately 60 l/hour of gas, a response time of only 7 seconds was achieved.

An embodiment of the invention will now be described in greater detail with reference to the accompanying drawing.

A storage container 1 comprises a reagent solution which is first supplied to the reference cell 3 of a photometer 4 by means of a pump 2. Such photometers are known in various constructions as 1-beam- or 2-beam-photometers and are described, for example, in German Patent Specification No. 967,633 or French Patent Specification No. 1,494,281. From said reference cell the reagent solution is continuously supplied to the inlet of a reaction chamber 5, approximately 20 cm$^3$/hour being supplied.

The gas to be examined, for example air, is supplied to the same inlet of the reaction chamber 5. The gaseous pollutants present in the air, so in the present example $Cl_2$, react with the reagent solution and produce its decolorization, the decolorization being the stronger as the amount of the pollutant in the air is higher. Approximately 60 liters of air per hour are transported through the reaction chamber.

The reagent solution decolorized in this manner is then passed via a first outlet 18 of the reaction chamber 5 through the measuring cell 6 of the photometer 4 and is then supplied again to the reaction chamber 5. At a second outlet 19 there occur both the air and the consumed reagent solution. The liquid is collected in a collection container 9, while the air is either exhausted to the atmosphere via a second pump 12, a condensate separator 14, a flow-meter 13 and a 3-way-cock 11, or is supplied again to the reaction chamber 5 as a so-called "zero gas" via an active-carbon filter 10.

The reaction chamber 5 comprises a vertical reaction track 16 to the lower inlet 15 to which there are supplied both the gas, for example, air, to be examined, and also the reagent solution from the reference cell 3, and the solution originating from the measuring cell 6 and containing the pollutant. Above the reaction track 16 is arranged a collection vessel 17 which constantly contains a certain quantity of the reagent solution. A first outlet 18, likewise vertical, leads to the input of the measuring cell 6. As a result, of this, a liquid column is formed above the outlet 18.

Above the collection vessel 17 is arranged another outlet 19 from which the remaining solution escapes and enters into the collection container 9. Since only a comparatively small quantity of fresh reagent is supplied — namely approximately 20 cm$^3$/hour as stated above— the consumption of fresh solution is very small. As a result of the arrangement according to the invention, the reagent solution flows in a closed cycle several times through the reaction track 16, the collection container 17 and the measuring cell 6, so that it is used optimum in that it contacts the gas several times. In proportion to the reagent solution derived from the storage container 1, an essentially larger throughput in the reaction chamber is obtained in this manner. The response time is thus maintained very short. As a result of the unused reagent solution which is supplied comparatively slowly, the liquid level in the reaction chamber rises up to a level at which the supplied quantity of liquid corresponds to the quantity taken up by the second outlet.

Since the decolorization of the reagent solution depends considerably on the quantity of the fresh solution supplied per unit of time and on the supplied quantity of air, it is necessary to keep these throughput quantities constant.

It has been demonstrated that with the method described an indication on the share of pollutant in the air or the change thereof is obtained already after 7 seconds.

What is claimed is:

1. A method for the continuous quantitative indication of pollutants in a gas, comprising the steps of taking a reagent solution from a storage container and first passing said reagent solution through a reference cell of a photometer, then mixing said reagent solution in a reaction chamber with the gas to be examined, said reagent solution being colorized or decolorized dependent on the concentration of the pollutant, then passing said reagent solution with said gas through the measuring cell of the photometer, determining the output voltage of the photometer to obtain an indication corresponding to the concentration of pollutant, supplying again to said reaction chamber a part of the reagent solution leaving said measuring cell and containing the pollutant and, finally, collecting said reagent solution in a collection container.

2. A method as in claim 1, wherein the remaining solution from said measuring cell is derived from a second outlet of said reaction chamber and is collected in a collection container.

3. A method as in claim 2, wherein gas present in the remaining reagent solution from said reagent solution is separated and said reagent solution is cleaned in an active-carbon filter and then supplied to the reaction chamber as "zero gas".

4. An apparatus for carrying out the method recited in claim 1, comprising:
  (a) a reagent storage container,
  (b) a photometer comprising a reference cell and a measuring cell, said measuring cell comprising input means for providing said reagent thereto and output means for removing said reagent therefrom, said reference cell comprising entry and exit means for providing said reagent thereto and removing said reagent therefrom,
  (c) indicator means connected to said photometer for determining the coloration of said reagent solution,
  (d) pumping means for transporting said reagent from said storage container to said entry means of said reference cell,
  (e) a reaction chamber communicating with said photometer, said reaction chamber comprising a vertically arranged reaction track and a collection vessel disposed above said reaction track, said collection vessel comprising an inlet, a first outlet, and a second outlet, said first outlet being connected to said input means of said measuring cell and said exit means of said reference cell and said output of said measuring cell being connected to said inlet of said collection vessel, and
  (f) a collection container for receiving said reactant, said second outlet of said collection vessel being connected to said input means of said measuring cell.

5. An apparatus as in claim 4, comprising a further pump, a condensate separator and a flowmeter, said flowmeter comprising an outlet that is connected to said inlet of said reaction chamber via an active-carbon filter, said further pump being connected to said second outlet of said reaction chamber.

6. An apparatus as in claim 5, comprising a 3-way-cock disposed between said flowmeter and said active-carbon filter.

7. An apparatus as in claim 4, comprising means for introducing said gas into said reaction chamber and mixing said gas and said reagent.

8. Apparatus for the continuous quantitative indication of pollutants in a gas, comprising means for taking a reagent solution from a storage container and first passing the reagent solution through a reference cell of a photometer, means for mixing the reagent solution in the reaction chamber with the gas to be examined, the reagent solution being colorized or decolorized dependent on the concentration of the pollutant, means for passing the reagent solution with the gas through the measuring cell of the photometer, means for determining the output voltage of the photometer to obtain an indication corresponding to the concentration of pollutant, means for supplying again to the reaction chamber a part of the reagent solution leaving the measuring cell and containing the pollutant, and means for collecting the reagent solution in the collection container.

* * * * *